United States Patent [19]
Fielding et al.

[11] 4,016,217
[45] Apr. 5, 1977

[54] PREPARATION OF PERFLUOROOLEFINES

[75] Inventors: Harold Crosbie Fielding, Northwich; Alfred John Rudge, Frodsham, both of England

[73] Assignee: Imperial Chemical Industries Limited, London, England

[22] Filed: Apr. 25, 1975

[21] Appl. No.: 571,770

Related U.S. Application Data

[63] Continuation of Ser. No. 41,164, May 25, 1970, abandoned, which is a continuation of Ser. No. 537,689, March 28, 1966.

[30] Foreign Application Priority Data

Apr. 8, 1965 United Kingdom ............ 14992/65

[52] U.S. Cl. ........................................ 260/653.1 R
[51] Int. Cl.² .................. C07C 17/26; C07C 19/08
[58] Field of Search ............................ 260/653.1 R

[56] References Cited

UNITED STATES PATENTS

| | | | |
|---|---|---|---|
| 2,918,501 | 12/1959 | Brehm et al. .................... | 260/653.3 |
| 3,083,238 | 3/1963 | Hauptschein et al. ...... | 260/653.1 T |
| 3,403,191 | 9/1968 | Graham ..................... | 260/653.1 R |

OTHER PUBLICATIONS

Graham, J. Org. Chem. 31, pp. 955–957 (1966).

*Primary Examiner*—D. Horwitz
*Attorney, Agent, or Firm*—Cushman, Darby & Cushman

[57] ABSTRACT

A process for making branched, internally-unsaturated liquid perfluoroolefins that are oligomers of tetrafluoroethylene and have an empirical formula $(C_2F_4)_n$ where $n$ is an integer of 4 to 7, comprising contacting tetrafluoroethylene under anhydrous conditions with at least one fluoride which is a source of fluoride ions, said fluoride being selected from the group consisting of the normal fluorides, acid fluorides and fluorosulphinates of the metals potassium, rubidium and caesium and normal fluorides of a tetraalkylammonium ion, at a temperature of 20° C to 170° C in the presence of an inert solvent selected from the group consisting of dimethylformamide, dimethyl sulphoxide, N-methyl pyrrolidone and hexamethylphosphoramide, and recovering said branched, internally-unsaturated liquid perfluoroolefins from the reaction medium.

12 Claims, No Drawings

PREPARATION OF PERFLUOROOLEFINES

This is a continuation of application Ser. No. 41,164 filed May 25, 1970, now abandoned; which is a continuation of Ser. No. 537,689 filed Mar. 28, 1966.

This invention relates to a method of making perfluoroolefins using tetrafluoroethylene as a starting point, particularly branched-chain internally unsaturated perfluoroolefins that are oligomers of tetrafluoroethylene.

Polyfluorinated organic compounds whose molecules are made up of chains of $>CF_2$ groups terminating in other halogenated groups or halogens, for example $-CF_3$, $-CCl_3$, $-SF_5$ and Cl are useful in various ways, for example as thermally stable solvents, dielectric fluids and evaporative coolants. Related compounds, in which the chains terminate in functional groups, for example carboxyl, and their derivatives are useful for their surface-active properties.

If it were possible to prepare from tetrafluoroethylene perfluoroolefins containing carbon chains of four or more atoms one would have available compounds potentially useful as thermally stable liquids, dielectric fluids and evaporative coolants and as starting materials for preparing perfluoroacids and other related compounds having potentially valuable properties. The object of the present invention is to prepare such olefins from tetrafluoroethylene.

Thus according to our invention we provide a process for making branched, internally unsaturated perfluoroolefins that are oligomers of tetrafluoroethylene comprising contacting tetrafluoroethylene with one or more fluorides of potassium, rubidium, caesium or of a quaternary ammonium radical under anhydrous conditions and recovering said branched, internally unsaturated perfluoroolefins.

The invention also provides novel branched and internally unsaturated perfluoroolefins that are oligomers of tetrafluoroethylene having the general formula $(C_2F_4)_n$ where n is an integer equal to at least 4.

The reaction is conveniently carried out at temperatures from 20° C to 170° C in the presence of an inert solvent, preferably from 50° C to 150° C depending on the fluoride and solvent employed. The reaction can also be carried out in the absence of a solvent, though less conveniently, for example at temperatures up to 700° C with potassium fluoride or caesium fluoride or at temperatures from about 150° C to 200° C with tetraethylammonium fluoride. It is advantageous to include a small proportion of a free-radical inhibitor in the reaction system, for example 0.1 to 0.50% by weight of the tetrafluoroethylene of α-pinene, in order to inhibit free-radical polymerization of the tetrafluoroethylene.

In this specification the term fluoride of potassium, rubidium or caesium is meant to include not only the normal fluorides KF, RbF and CaF but also acid fluorides of potassium, rubidium and caesium, for example KF.HF, CaF.Hf, and fluorosalts that are sources of fluoride ions for example fluorosulphinates $KSO_2F$ and $CaSO_2F$. Examples of quaternary ammonium fluorides are tetraethylammonium fluoride and tetramethylammonium fluoride. Tetralkylammonium fluorides containing different alkyl groups in the same molecule can be used, also quaternary ammonium fluorides containing both alkyl and aryl groups. The proportion of fluoride generally employed in the reaction is from 0.10 to 15% by weight of the tetrafluoroethylene.

Suitable solvents include dimethylformamide, N-methyl pyrrolidene, hexamethylphosphoramide, dimethyl sulphoxide, the dimethyl ethers of ethylene glycol and of diethylene glycol. The quantity of solvent is not critical but is preferably sufficient to maintain the fluoride in a well-agitated suspension. The fluoride should be dry and those that are insoluble are preferably in a finely divided state such as that produced by ball-milling.

The reaction may be carried out at any convenient pressure, preferably above atmospheric pressure but not necessarily so. The reaction is normally complete in from 1 to 12 hours at the higher end of the preferred temperature range, but at the lower end it may be extended well beyond 12 hours. The shorter reaction times are preferred. The novel perfluoroolefins of the invention, which we refer to as oligomers of tetrafluoroethylene, are not straight-chain compounds and do not possess terminal unsaturation. They are on the contrary branched and internally unsaturated. They have the empirical formula $(C_2F_4)_n$, where n is an integer equal to at least 4. Formed in the highest yield by the process of the invention are those where n is from 4 to 7, that is to say the tetramer, pentamer, hexamer and heptamer, but products for which n is greater than 7 are also formed though in lower yield. Available experimental evidence does not so far enable one to present precise structural formulae for each of the oligomers, but it has shown that they are internally unsaturated and contain a high proportion of $CF_3$ groups from which it is certain that the molecules are branched. The main components of the tetramer, pentamer, hexamer and heptamer fraction of the reaction products have been separated therefrom by vapour-phase chromatography and investigated. Elementary analysis has shown each to have the empirical formula $(C_2F_4)_n$ and vapour density determinations have shown n to be 4, 5, 6 and 7 respectively. Mass-spectrographic analysis of each oligomer has shown the presence of a high proportion of $CF_3$ groups and only weak mass-peaks for the parent ion have been observed. Nuclear magnetic resonance spectra observations have confirmed that the molecules are branched. The oligomers resist oxidation by aqueous potassium or sodium permanganates but are oxidated by potassium permanganate in acetone to give small fragments such as $CF_3H$ and $CF_3CF_2COOH$.

The reaction mechanism leading to the formation of the oligomers is not yet fully understood but it is possible that tetrafluoroethylene reacts with a pentafluoroethyl anion to give a further anion which isomerises and then undergoes further reaction with tetrafluoroethylene. Growing in this way the anion can lose a fluoride ion at an appropriate stage to yield an oligomer. Thus the structure of the pentamer could be

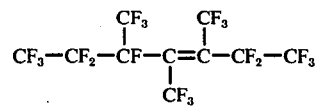

which is not incompatible with the chemical and physical evidence available and can be arrived at by anion formation and isomerisation as hereinbefore postulated.

The invention is illustrated by Examples 1–15 and 17–19. Example 16 is a comparison experiment in which the reaction was carried out without any fluoride present and it can be seen that no oligomers were formed. Examples 4–16 are summarised in the Table.

EXAMPLE 1

Tetrafluoroethylene (20 g.) was distilled into an autoclave containing anhydrous dimethylformamide (50 ml.) and anhydrous potassium fluoride (2 g.). The autoclave was then heated to 150° C with stirring. After 3 hours the internal pressure had dropped from 350 to 25 lb/sq. inch gauge. The contents of the vessel were then separated into a pale-yellow layer and a dark upper layer. The lower layer (13 g.) was washed with water, dried and distilled to give a mixed perfluoroolefin fraction boiling mainly between 110° and 130° C, and exhibiting unsaturation in the infra-red region at 6.1 microns (1640 cm.$^{-1}$).

EXAMPLE 2

An autoclave containing anhydrous dimethylformamide (200 ml.) and anhydrous KF (6 g.) was pressurised, at room temperature, with tetrafluoroethylene to 200 lb/sq. inch gauge. The mixture was then heated, with stirring, to 130° C. After 2½ hours the pressure in the system had fallen from 350 to 80 lb/sq. inch gauge. At this stage the system was repressurised with tetrafluoroethylene to 350 lg/sq. inch gauge and the reaction continued. After a further 3 hours the system was again repressurised to 350 lb/sq. inch gauge and after a further 3 hours the reaction was terminated. The lower layer was then separated from the dimethylformamide layer. After washing with water and drying 60 g. of perfluoroolefins remained, boiling mainly within the range 110°–130° C.

EXAMPLE 3

Dry caesium fluoride (5 g.), dry dimethylformamide (150 mls.) and α-pinene (0.10 g.) were ground in a ball mill for 12 hours. The slurry was then transferred to a dry 500 mls. stainless steel stirred autoclave which was then swept out with dry nitrogen. The reaction mixture was stirred and heated to 60° C and the autoclave pressurised with tetrafluoroethylene to 50 lb/sq. inch gauge. An exothermic reaction took place and raised the temperature to 70° C whereupon the pressure fell to approximately atmospheric. The reaction system was re-pressurised repeatedly with tetrafluoroethylene each time the rate of the exothermic reaction decreased until the equivalent of 350 lb/sq. inch was being charged to the autoclave at each re-pressurisation.

After 4 hours of this procedure, by which time the accumulated pressure drop had reached 1200 lb/sq. inch, the autoclave was cooled and the products discharged. The oligomer layer was separated from the solvent, washed with a little dimethylformamide, then with water and finally dried over anhydrous sodium sulphate.

The oligomer mixture (250 g.) was distilled and the following fractions were collected.

| | | | |
|---|---|---|---|
| (i) | b.pt. | <90° C | 2.3 g. |
| (ii) | | 90 – 92° C | 27.0 |
| (iii) | | 92 – 130° C | 22.0 |
| (iv) | | 130 – 132° C | 115.0 |
| (v) | | >132° C | 80.0 |

Fraction (ii) was mainly the tetramer $(C_2F_4)_4$; fraction (iv) mainly the pentamer $(C_2F_4)_5$; whilst fraction (iii) was a mixture of tetramer and pentamer. Fraction (v) was mainly the hexamer $(C_2F_4)_6$, heptamer $(C_2F_4)_7$ and higher oligomers.

EXAMPLES 4–16

The results of the experiments on which these Examples are based are summarised in the Table. The reactants were charged into a 500 mls. stainless steel autoclave and the reaction carried out in a manner similar to that described in Example 3. In all the experiments the weight of fluoride was 5 g. and the volume of solvent 150 mls. except in experiment 16 where no fluoride was present, and in experiments 10 and 14 where the volume of solvent was 100 mls. Diglyme, the solvent used in experiment 14 is the dimethylether of diethylene glycol. Extensive side reactions occurred between tetrafluoroethylene and diglyme and dimethoxyethane in experiments 14 and 15 respectively.

Table

| Expt. | Solvent | Fluoride | Temperature °C | Time hours | Total pressure drop lb/sq.inch | Oligomers formed grammes |
|---|---|---|---|---|---|---|
| 4 | DMF | $C_5F$ | 80 | 6 | 1500 | 265 |
| 5 | " | KF | 125 | 6 | 800 | 140 |
| 6 | " | Et$_4$NF | 110 | 6 | 500 | 100 |
| 7 | " | KM . MF | 135 | 6 | 500 | 115 |
| 8 | " | KSO$_2$F | 140 | 4 | 400 | 85 |
| 9 | " | CsSO$_2$F | 110 | 4 | 300 | 70 |
| 10 | " | $C_5F$ | 60 | 1 | 1100 | 220 |
| 11 | NMP | " | 100 | 4 | 800 | 135 |
| 12 | DMSO | " | 100 | 4 | 600 | 110 |
| 13 | HMP | " | 100 | 4 | 1200 | 230 |
| 14 | DG | " | 120 | 6 | 800 | 80 |
| 15 | DME | " | 120 | 6 | 600 | 60 |
| 16 | DMF | none | 150 | 4 | none | none |

In the above Table
DMF    represents dimethylformamide
NMP    represents N-methyl pyrrolidone
DMSO   represents dimethyl sulphoxide
HMP    represents hexamethylphosphoramide
DG     represents diglyme
DME    represents 1,2-dimethoxyethane

EXAMPLE 17

This illustrates a reaction at atmospheric pressure. Tetrafluoroethylene was bubbled at atmospheric pressure through a vigorously stirred slurry of caesium fluoride (10 g.) in dimethyl-formamide (100 mls.) at 120° C. A small amount of a colourless liquid collected as a lower layer, and was identified by vapour-phase chromatography and infra-red absorption spectra as a mixture of oligomers $(C_2F_4)_n$ where $n$ is 4 to 6.

EXAMPLE 18

Tetrafluoroethylene was passed over a static bed of caesium fluoride contained in a stainless steel tube at 700° C. Among the reaction products were mixed perfluorobutenes formed by pyrolysis of tetrafluoroethylene and a small amount of a liquid whose main constituent was identified by mass-spectrograph measurements as the tetramer $(C_2F_4)_4$.

EXAMPLE 19

This illustrates a reaction under pressure in the absence of solvent. Tetrafluoroethylene (20 g.) was distilled on to dry tetraethylammonium fluoride (2.5 g.) contained in a dry 50 ml. autoclave at −80° C. The reaction system was then slowly heated to 150° C, and maintained at this temperature for 4 hours. After cooling to room temperature unreacted tetrafluoroethylene was vented to atmosphere. Approximately 2.0 g. of liquid products remained in the autoclave and were shown to be a mixture of tetrafluoroethylene oligomers consisting mainly of tetramer and pentamer.

What we claim is:

1. A process for making branched, internally-unsaturated liquid perfluoroolefins that are oligomers of tetrafluoroethylene and have an empiricial formula $(C_2F_4)_n$ where $n$ is an integer of 4 to 7, comprising contacting tetrafluoroethylene under anhydrous conditions with at least one fluoride which is a source of fluoride ions, said fluoride being selected from the group consisting of the normal fluorides, acid fluorides and fluorosulphinates of the metals potassium, rubidium and caesium and normal fluorides of a tetraalkylammonium ion, at a temperature of 20° C to 170° C in the presence of an inert solvent selected from the group consisting of dimethylformamide, dimethyl sulphoxide, N-methyl pyrrolidone and hexamethylphosphoramide, and recovering said branched, internally-unsaturated liquid perfluoroolefins from the reaction medium.

2. A process as claimed in claim 1 in which the proportion of fluoride in the reaction system is from 0.10% to 15% by weight of the tetrafluoroethylene.

3. A process according to claim 1 wherein the tetrafluoroethylene is contacted at a temperature from 50° C to 150° C with from 0.10 to 15% by weight of fluoride in the presence of dimethylformamide.

4. A process according to claim 1 wherein the tetrafluoroethylene is contacted at a temperature from 50° C to 150° C with from 0.10 to 15% by weight of caesium or potassium fluoride in the presence of dimethylformamide.

5. A process as claimed in claim 1 in which the reaction is carried out at above atmospheric pressure.

6. A process as claimed in claim 1 wherein the fluoride is the acid fluoride of potassium, rubidium or caesium.

7. A process as claimed in claim 1 wherein the fluoride is the fluorosulphinate of potassium or caesium.

8. A process as claimed in claim 1 wherein the tetraalkylammonium ion is the tetraethyl or tetramethylammonium ion.

9. A process as claimed in claim 1 wherein the pressure is about 350 psig.

10. A process as claimed in claim 1 wherein a free-radical inhibitor is included in the reaction mixture.

11. A process as claimed in claim 10 wherein the free-radical inhibitor α-pinene is used in the reaction mixture at a concentration of 0.1% to 0.5% by weight of the tetrafluoroethylene.

12. A process as claimed in claim 1 wherein the fluoride is selected from potassium fluoride and tetraalkylammonium fluorides wherein the alkyl is methyl or ethyl and the solvent is selected from dimethylformamide and dimethylsulphoxide.

* * * * *